(12) United States Patent  (10) Patent No.: US 8,273,041 B2
Goumas  (45) Date of Patent: Sep. 25, 2012

(54) ARM CRADLE

(75) Inventor: Douglas Goumas, Bedford, NH (US)

(73) Assignee: G Force Braces, LLC, Bedford, NH (US)

( * ) Notice: Subject to any disclaimer, the term of this patent is extended or adjusted under 35 U.S.C. 154(b) by 0 days.

(21) Appl. No.: 13/091,419

(22) Filed: Apr. 21, 2011

(65) Prior Publication Data

US 2011/0192403 A1   Aug. 11, 2011

Related U.S. Application Data

(63) Continuation-in-part of application No. 12/424,805, filed on Apr. 16, 2009, now Pat. No. 8,043,241.

(60) Provisional application No. 61/199,094, filed on Nov. 12, 2008.

(51) Int. Cl.
*A61F 5/00* (2006.01)
*A61F 5/37* (2006.01)

(52) U.S. Cl. .............. 602/4; 602/20; 602/21; 128/845; 128/846; 128/878; 128/892

(58) Field of Classification Search ............. 602/4, 20, 602/21; 128/845, 846, 869, 878, 881, 892
See application file for complete search history.

(56) References Cited

U.S. PATENT DOCUMENTS

| | | | |
|---|---|---|---|
| D247,311 S | 2/1978 | Carter | |
| 4,173,048 A | 11/1979 | Varaney | |
| 4,186,738 A | 2/1980 | Schleicher et al. | |
| 4,210,317 A | 7/1980 | Spann et al. | |
| 4,270,235 A | 6/1981 | Gutmann | |
| 4,375,809 A | 3/1983 | Meals | |
| D287,641 S | 1/1987 | Schaefer | |
| D296,932 S | 7/1988 | Tranghese | |
| 4,896,660 A | 1/1990 | Scott | |
| D321,562 S | 11/1991 | Ljungvall | |
| 5,418,991 A | 5/1995 | Shiflett | |
| D362,072 S | 9/1995 | Sternberg | |
| 5,584,303 A | 12/1996 | Walle | |
| 5,603,692 A | 2/1997 | Maxwell | |
| D382,057 S | 8/1997 | Swedberg et al. | |
| 5,716,334 A | 2/1998 | Wade | |
| D396,291 S | 7/1998 | Bakes | |
| 5,782,244 A | 7/1998 | Kostich | |
| D413,982 S | 9/1999 | Swedberg et al. | |
| D415,281 S | 10/1999 | Swedberg et al. | |
| D422,362 S | 4/2000 | Ames | |
| 6,047,420 A | 4/2000 | Priester, III et al. | |
| D426,307 S | 6/2000 | Swedberg et al. | |
| D447,568 S | 9/2001 | Hall et al. | |

(Continued)

*Primary Examiner* — Patricia Bianco
*Assistant Examiner* — Keri J Nelson
(74) *Attorney, Agent, or Firm* — Lipsitz & McAllister, LLC

(57) ABSTRACT

An arm cradle for holding and stabilizing an arm of a post-operative shoulder surgery patient is provided. The arm cradle has a cradle body having a first concave section adapted to accept at least a portion of an upper arm of a patient and a second concave section adapted to accept at least a portion of a lower arm of the patient. The first concave section and the second concave section may be arranged at an obtuse angle with respect to one another. A fabric cover may be provided for the cradle body. One or more straps may be affixed to one of the cradle body or the fabric cover and used to secure the arm cradle to the patient and/or to secure the arm of the patient in the arm cradle.

20 Claims, 8 Drawing Sheets

U.S. PATENT DOCUMENTS

| | | |
|---|---|---|
| D475,757 S | 6/2003 | Silverman et al. |
| 6,691,353 B2 | 2/2004 | Fuhriman |
| 7,017,215 B1 | 3/2006 | Singer et al. |
| 7,189,213 B1 | 3/2007 | Weber |
| 7,244,239 B2 | 7/2007 | Howard |
| 7,441,293 B1 | 10/2008 | Singer et al. |
| D624,344 S | 9/2010 | Kashey |
| 2009/0119845 A1* | 5/2009 | Bastien et al. ............ 5/646 |

\* cited by examiner

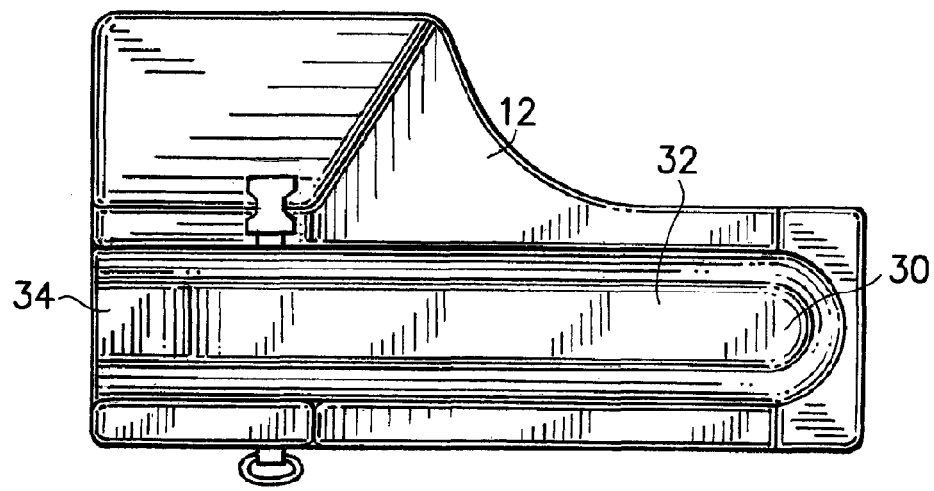
FIG.5
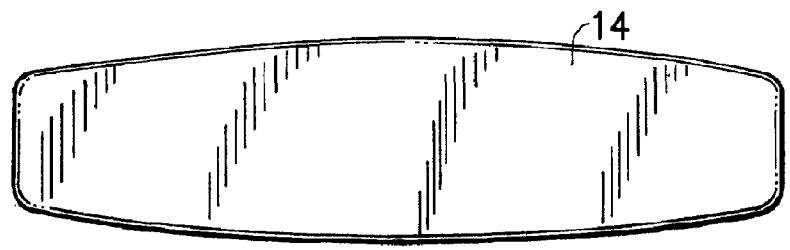
FIG.6
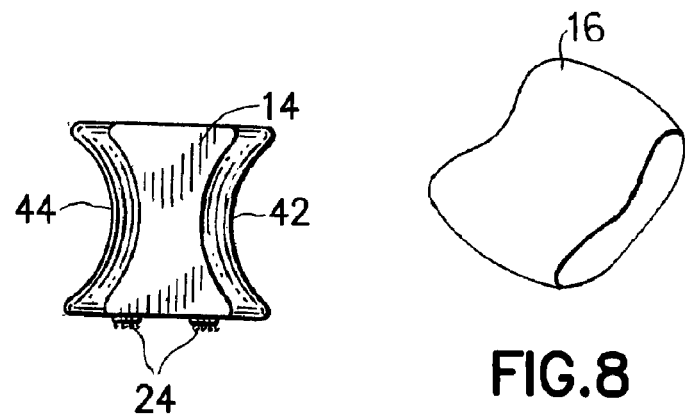
FIG.7
FIG.8

ARM CRADLE

This application is a continuation-in-part of commonly owned co-pending U.S. patent application Ser. No. 12/424, 805 filed on Apr. 16, 2009, which claims the benefit of U.S. provisional patent application No. 61/199,094 filed on Nov. 12, 2008, both of which are incorporated herein and made a part hereof by reference.

BACKGROUND OF THE INVENTION

The present invention relates to supports for patients recovering from shoulder surgery. More specifically, the present invention relates to systems, apparatus, and methods that provide support for a patient's arm which enables shoulder surgery patients to sleep in a supine position in a stable manner and which include a cradle portion adapted to be worn as a sling during waking hours.

The prior art discloses several types of support pillows for shoulder surgery patients. However, none of the prior art devices provide support for the surgically repaired arm and shoulder while at the same time restricting patient movement (e.g., rolling over or shifting onto one side) in order to prevent injury or damage to the surgically repaired shoulder during sleep. Further, none of the prior art support pillows are convertible into a sling for use by the patient during waking hours.

Accordingly, it would be advantageous to provide a support device for shoulder surgery patients that supports the surgically repaired shoulder and arm while at the same time restricting patient movement. It would also be advantageous if a portion of such a support device could be adapted to be worn as a sling during waking hours.

The systems, methods and apparatus of the present invention provide the foregoing and other advantages.

SUMMARY OF INVENTION

The present invention relates to a support system for surgical patients, a convertible support for surgical patients, and a method for providing a convertible support for surgical patients.

In one example embodiment, a support system for surgical patients is provided. The support system comprises an arm cradle adapted to hold a first arm of a patient at an angle when the patient is in a supine position and a side bolster with a first side adapted to be positioned against a side of a patient opposite the arm cradle. The side bolster is adapted to stabilize the patient in the supine position.

The support system may further comprise a mat. The mat may be positioned on a bed, the floor, or other flat surface adapted for sleeping. The arm cradle and the side bolster may be temporarily secured to the mat. In addition, a T-shaped strap may be provided for securing the arm cradle to the mat and the patient. The T-shaped strap may comprise a first end adapted to be secured to the arm cradle, a first length of strap for encircling a waist of the patient, and a second length of strap adapted to be secured to the mat which is attached to the first length and perpendicular to the first length.

The support system may also comprise a head support secured to the mat and adapted to support a head of the patient.

In a further example embodiment, the arm cradle may comprise a first section adapted to accept an upper arm of the patient, and a second section adapted to accept a lower arm of the patient. The arm cradle may further comprise a base portion. The first section may be angled with respect to the base portion and the second section may be angled with respect to the first section. For example, the first section may be at an angle in a first range between 0 and 30 degrees with respect to the base portion and the second section may be at an angle in a second range between 90 and 170 degrees with respect to the first section.

In another example embodiment, the angle between the first section and the base portion may be adjustable within the first range and the angle between the second section and the first section may be adjustable within the second range.

The arm cradle may also comprise a third section adapted to support a hand of the patient. The third section may be angled with respect to the second section. For example, the third section may be at an angle in a third range between 120 and 150 degrees with respect to the second section. The angle between the third section and the second section may be adjustable within the third range.

In addition, one or more straps may be fixed to the arm cradle for securing the first arm of the patient in the arm cradle.

In a further example embodiment, the arm cradle may be adapted to be worn as a sling when the patient is ambulatory. In such an embodiment, one or more straps may be affixed to the arm cradle and configured to support the arm cradle for use as a sling. For example, the one or more straps may comprise a shoulder strap and a waist strap. Additionally, the one or more straps may be adapted to secure the arm cradle to the mat when the patient is in the supine position.

The side bolster may have a second side adapted to conform to a second arm of the patient in an extension position. The side bolster may have a second side which is symmetrical with the first side, enabling use of the side bolster on either side of a patient. At least portions of the first side and the second side of the side bolster may be concave.

The patient may comprise a shoulder surgery patient. The angle at which the arm cradle holds the first arm of the patient in the supine position may be chosen so as to speed recovery from the shoulder surgery while immobilizing the shoulder during sleep.

The present invention also provided a convertible support for shoulder surgery patients. In one example embodiment, the convertible support may comprise an arm cradle which is adapted to hold an arm of a patient at an angle when the patient is in a supine position and adapted to be worn as a sling when the patient is ambulatory. Straps affixed to the arm cradle may be configured to support the sling when the patient is ambulatory. The arm cradle of the convertible support may include additional features as discussed above in connection with the support system.

The present invention also includes a method for providing a convertible support system for shoulder surgery patients. In one example embodiment, the method may comprise providing an arm cradle adapted to hold a first arm of a patient at an angle when the patient is in a supine position and adapted to be worn as a sling when the patient is ambulatory, as well as providing straps affixed to the arm cradle configured to support the sling when the patient is ambulatory. The method may further comprise providing a side bolster with a first side adapted to be positioned against a side of a patient opposite the arm cradle, where the side bolster adapted to stabilize the patient in the supine position. The method may include providing additional features and elements discussed above in connection with the support system.

The present invention also relates to an embodiment of an arm cradle for holding and stabilizing an arm of a post-operative shoulder surgery patient. This embodiment may be used with or without the side bolster or mat discussed above.

In one example embodiment of such an arm cradle in accordance with the present invention, the arm cradle may comprise a cradle body having a first concave section adapted to accept at least a portion of an upper arm of a patient and a second concave section adapted to accept at least a portion of a lower arm of the patient. The first concave section and the second concave section may be arranged at an obtuse angle with respect to one another. A fabric cover may be provided for the cradle body. One or more straps may be affixed to one of the cradle body or the fabric cover and used to secure the arm cradle to the patient and/or to secure the arm of the patient in the arm cradle.

The arm cradle may be designed to at least partially encompass the upper and lower arms of the patient. For example, the first concave section of the arm cradle may be of a depth corresponding to at least one-half to at least three-quarters of a diameter of the upper arm of the patient. The second concave section may be of a depth corresponding to at least one-half to at least three-quarters of a diameter of the lower arm of the patient.

The fabric cover may be removable. For example, the fabric cover may be provided with a zipper or other fastening means (such as Velcro®, snaps, or the like) to enable it to be removed for washing or replacement.

The cradle body may be comprised of a resilient foam material. For example, the cradle body may be produced in one-piece via injection molding or hot-knife machined from a block of resilient foam material.

In a further example embodiment of the present invention, the arm cradle may further comprise a base portion. The first concave section may be angled with respect to the base portion. The first concave section may be at an angle in a first range between 0 and 30 degrees with respect to the base portion. The obtuse angle between the first concave section and the second concave section may be in a second range between 90 and 170 degrees.

The cradle body may further comprise a third concave section adapted to accept at least a portion of a hand of the patient. The third concave section may be of a depth corresponding to at least one-half to at least three-quarters of a thickness of the hand of the patient. The third concave section may be angled with respect to the second concave section. The third concave section may be at an angle in a third range between 120 and 150 degrees with respect to the second concave section.

The cradle body may be adapted to hold the arm of the patient at an angle when the patient is in a supine position and adapted to be worn as a sling when the patient is ambulatory. The base portion has a flat bottom adapted to abut against one of a bed, a floor, a mat, or a flat surface when the patient is in the supine position.

The one or more straps may comprise one or more first straps for securing the arm of the patient in the arm cradle, and one or more second straps for securing the arm cradle to the patient.

The one or more first straps may comprise at least one strap bridging opposite sides of the second concave section.

The one or more second straps may comprise a shoulder strap with one strap end affixed to a front section of the arm cradle and a second strap end affixed to a rear section of the arm cradle, the shoulder strap having an adjustable length sufficient to loop over a shoulder of the patient. The one or more second straps may further comprise an adjustable waist strap adapted to encircle the waist of a patient.

In a further example embodiment, an inner side of the cradle body abutting a body of the patient may be contoured to conform to the body of the patient. A portion of the inner side of the cradle body may progressively widen from a back section of the cradle body towards a front section of the cradle body.

The present invention also includes a method for supporting an arm of a patient. In one example embodiment, the method comprises providing a cradle body having a first concave section adapted to accept at least a portion of an upper arm of a patient and a second concave section adapted to accept at least a portion of a lower arm of the patient. The first concave section and the second concave section may be arranged at an obtuse angle with respect to one another. A fabric cover for the cradle body is also provided. One or more straps affixed to one of the cradle body or the fabric cover may also be provided. At least the portion of the upper arm is then positioned in the first concave section and at least the portion of the lower arm is positioned in the second concave section. The arm cradle can then be secured to the patient (and/or the arm of the patient can be secured in the arm cradle). The method may include providing additional features and elements discussed above in connection with the arm cradle itself.

BRIEF DESCRIPTION OF THE DRAWINGS

The present invention will hereinafter be described in conjunction with the appended drawing figures, wherein like reference numerals denote like elements, and:

FIG. 5 shows a top plan view of an example embodiment of an arm cradle in accordance with the present invention;

FIG. 6 shows a top plan view of an example embodiment of a side bolster in accordance with the present invention;

FIG. 7 shows a front elevational view of an example embodiment of a side bolster in accordance with the present invention;

FIG. 8 shows an example embodiment of an optional head support in accordance with the present invention.

DETAILED DESCRIPTION

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The present invention relates to a support system for surgical patients, a convertible support for surgical patients, and a method for providing a convertible support for surgical patients. While the present invention is described in detail below in connection with shoulder surgery patients, those skilled in the art will appreciate that the present invention may be used (or easily adapted for use) with patients recovering from other types of surgeries and/or injuries, such as upper arm surgeries or injuries, lower arm surgeries or injuries, elbow surgeries or injuries, hand surgeries or injuries, shoulder injuries, and any other injuries or surgeries that would require a patient to use a sling and to remain immobilized while sleeping.

Figure 1:
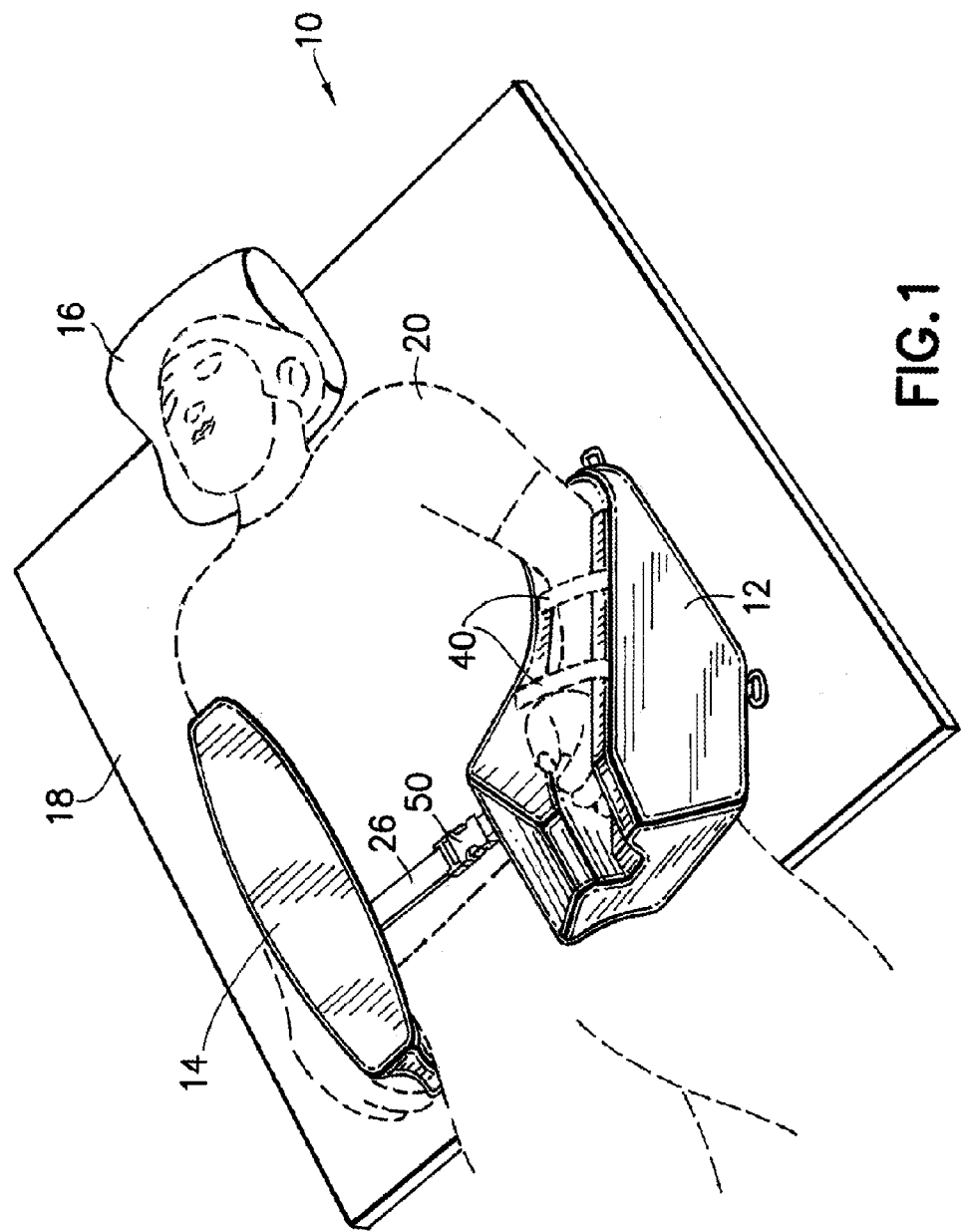
FIG. 1 shows an example embodiment of a support system in accordance with the present invention.
Figure 2:
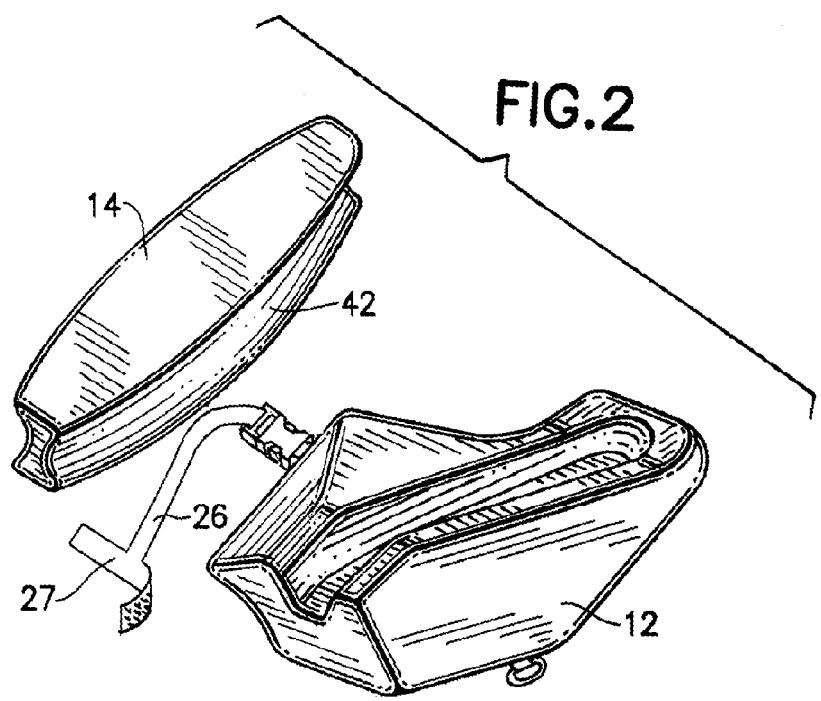
FIG. 2 shows a perspective view of example embodiments of an arm cradle and side bolster in accordance with the present invention.
Figure 4:
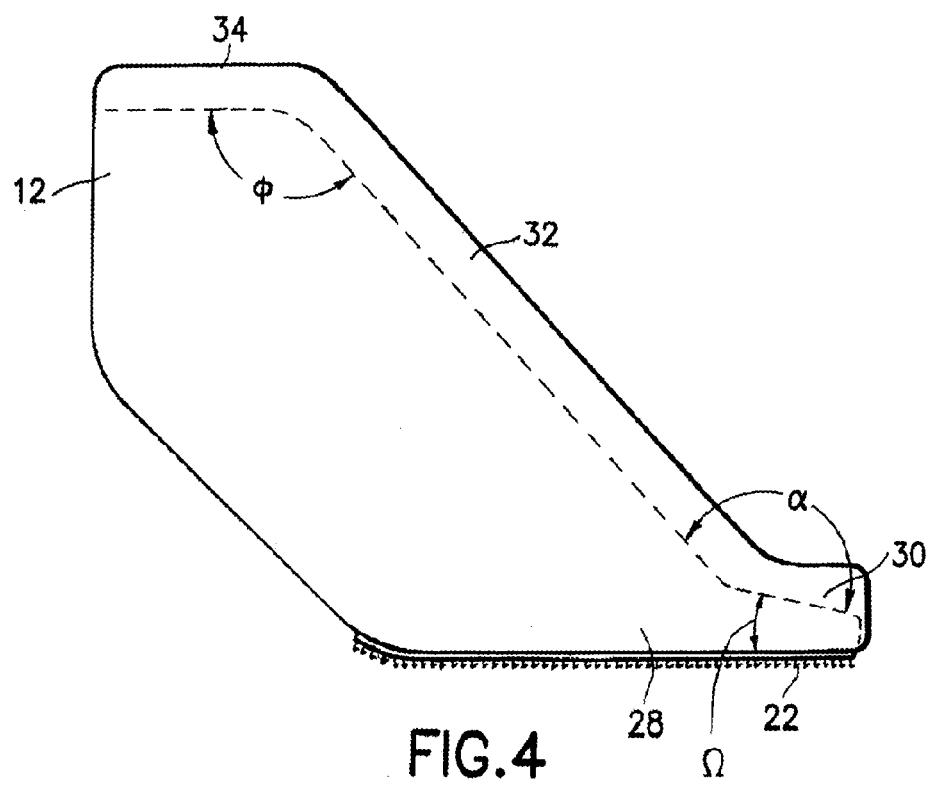
FIG. 4 shows a side view of an example embodiment of an arm cradle in accordance with the present invention.

As shown in FIG. 1, the support system 10 may comprise four portions, including an arm cradle 12, a side bolster 14, an optional head support 16, and an optional mat 18. FIG. 2 shows a perspective view of the arm cradle 12 and side bolster 14. FIG. 4 shows a side view of the arm cradle 12. FIG. 5 shows a top plan view of the arm cradle 12. FIG. 6 shows a top plan view of the side bolster 14. FIG. 7 shows a front elevational view of the side bolster 14.

As can be seen from the Figures, the arm cradle 12 is designed and adapted to hold an arm of a patient at an angle conducive to recovery from shoulder surgery when the patient 20 is in a supine position. The side bolster 14 is designed and adapted to conform to a side of a patient's body and to be positioned against a side of the patient opposite the side of the arm cradle 12 (e.g., with the patient 20 situated between the arm cradle 12 and the bolster 14 as shown in FIG. 1). The optional head support 16 is designed and adapted to conform to the back of a patient's head so as to support the head when the patient 20 is in the supine position. The arm cradle 12, side bolster 14, and optional head support 16 may also be adapted to be positioned on and secured to the mat 18 in a temporary manner.

For example, the arm cradle 12, side bolster 14, and optional head support 16 may all include a bottom portion covered, at least in part, by a Velcro® type material (i.e., hook and loop fasteners) adapted to interlock with a corresponding material provided on at least corresponding sections of a surface of the mat 18. FIG. 4 shows Velcro® strips 22 on the bottom of the arm support 12 and FIG. 7 shows Velcro® strips 24 on the bottom of the side bolster 14. Alternatively, the entire mat 18 may be covered with a corresponding Velcro®-like material so that the positioning of arm cradle 12, side bolster 14, and head support 16 can be varied as needed to conform to the patient's body type and comfort requirements. Other means of securing the arm cradle 12, side bolster 14, and head support 16 to the mat 18 may be used as would be apparent to those skilled in the art.

The arm cradle 12 may be made of a resilient foam material having a stable base portion 28. As discussed above, this base portion may be adapted to be temporarily affixed to the optional mat portion (e.g., via Velcro® strips 22). As shown in FIGS. 4 and 5, the arm cradle 12 may also include a first section 30 adapted to accept at least a portion of an upper arm of a patient 20. The first section 30 may be angled slightly with respect to the base portion 28. The angle $\Omega$ between the first section and the base section portion may be between 0 and 30 degrees. In one embodiment, the angle $\Omega$ between the first section and the base portion may be adjustable. The arm cradle 12 may also include a second section 32 adapted to accept at least a portion of a lower arm of the patient 20. This second section 32 may be at an angle $\alpha$ with respect to the first section 30, in order to support the patient's arm with a bend in the elbow. The angle $\alpha$ of the second section 32 with respect to the first section 30 may be between 90 to 170 degrees. In one example embodiment, the angle $\alpha$ between the second section 32 and the first section 30 may be adjustable. The arm cradle 12 may also include a third section 34 adapted to support at least a portion of a hand of the patient 20. This third section 34 may be at an angle $\phi$ to the second section 32. For example, the angle $\phi$ may be between approximately 120 to 150 degrees, and may be adjustable within this range. The angles may be set depending on the nature of the surgery performed, the optimal recovery position, the patient's unique physiology, patient comfort, or the like. The first, second, and third sections 30, 32, and 34 may be concave and/or contoured to accept the corresponding upper arm, lower arm, and hand of the patient 20.

The arm cradle 12 may be designed to at least partially encompass the upper and lower arms of the patient. For example, the first concave section 30 of the arm cradle may be of a depth corresponding to at least one-half to at least three-quarters of a diameter of the upper arm of the patient. The second concave section 32 may be of a depth corresponding to at least one-half to at least three-quarters of a diameter of the lower arm of the patient. The third concave section 34 may be of a depth corresponding to at least one-half to at least three-quarters of a thickness of the hand of the patient.

The arm cradle 12 is adapted to hold the arm and shoulder of the patient 20 in a comfortable and secure position during sleep in a supine position. Straps 40 may be provided to secure the arm in the arm cradle 12.

The side bolster 14 may also be made of a resilient foam material. As discussed above, a bottom portion of the side bolster 14 may be adapted to be temporarily secured to the optional mat 18 (e.g., via Velcro® strips 24). The side bolster 14 may comprise an elongated piece of foam material with a first side 42 adapted to be positioned against the side of the patient's body opposite the side of the body having the surgically repaired shoulder. A second side 44 of the side bolster 14 may be adapted to conform to an extended arm of the patient. The first and second sides 42, 44 may be concave, as shown in FIG. 7. The first and second sides 42, 44 may be identical, enabling use on either side of the patient. The side bolster 14 prevents a post-surgical patient 20 from rolling over during sleep, which could potentially damage the surgically repaired shoulder.

A T-shaped belt or strap 26 may also be provided, which is adapted to secure the arm cradle 12 to the mat 18 and the patient during sleep. One end of the T-strap may attach to a portion of the arm cradle 12 near the third section 34, e.g., via buckle 50 or a Velcro® connection. The buckle 50 may be attached to the arm cradle 12 via a short length of strap as shown in the Figures, or alternatively buckle 50 be secured directly to the arm cradle 12. A first length of the strap 26 may encircle the patient's waist with a second length (T-portion 27 shown in FIG. 2) secured to the mat 18 via Velcro® or similar material. The second length 27 is attached to the first length perpendicular to the first length of strap 26.

Figure 3:
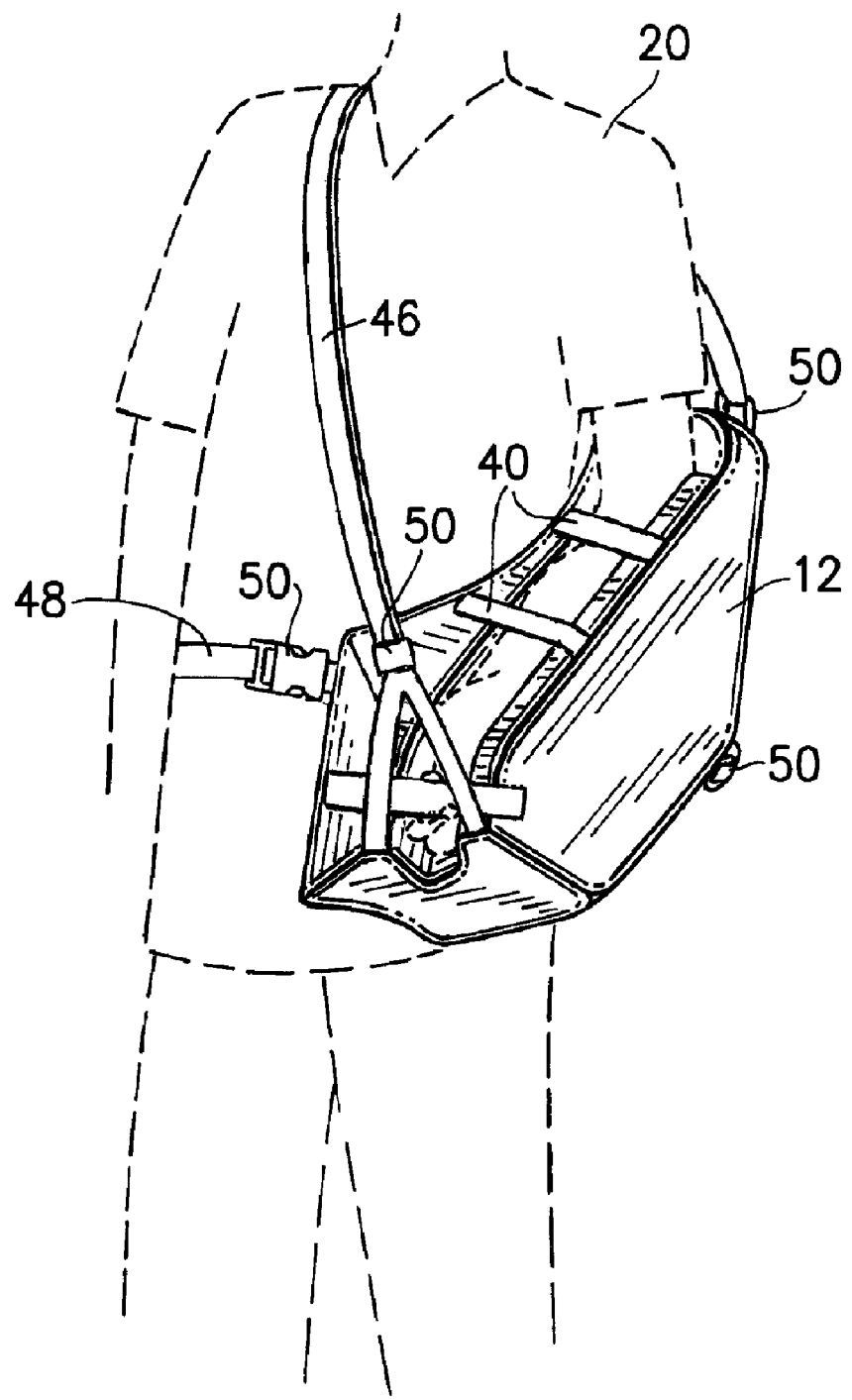
FIG. 3 shows an example embodiment of an arm cradle worn as a sling in accordance with the present invention.

The arm cradle 12 may also be adapted to be worn as a sling during waking hours, as shown in FIG. 3. For example, the T-strap may be used to secure the arm cradle 12 to the patient when used as a sling (e.g., the ends of T-portion 27 may be secured to additional buckles 50 on the arm cradle 12. Alternatively, the arm cradle 12 may include additional straps 46, 48 and buckles 50 which can be configured so as to secure the arm cradle 12 to the patient 20 enabling the arm cradle 12 to be worn as a sling. For example, strap 46 may comprise a shoulder strap that is affixed to the front and rear of the arm cradle 12, and the strap 48 may encircle the patient's waist and be affixed to the arm cradle at buckles 50 as shown in FIG. 7. The strap 48 may be connected to the arm cradle 12 at the same buckle 50 used to connect the T-strap 26. Thus, the arm cradle 12 may be secured to the mat 18 and used to stabilize the patient's arm during sleep as discussed above, and then, due to the temporary Velcro® type attachment, removed from the mat 18 and worn as a sling during waking hours. Advantageously, the patient 20 can move from sleeping in bed to walking around without the need to remove the arm from the arm cradle 12, maintaining immobility of the injured arm/shoulder during this process. Such immobility during the surgical recovery process is advantageous, especially in the early stages of recovery immediately following surgery.

It should be appreciated that all straps (including the T-strap 26, T-strap portion 27, shoulder strap 46, and waist strap 48) may be adjustable to fit different patient sizes and to provide for variable positioning of the arm cradle 12. Also, those skilled in the art will appreciate that the configuration, location, and number of different straps and buckles may be provided and are within the scope of the invention.

The optional head support 16 may also be made of a resilient foam material. As shown in FIG. 8, the head support 16 may have a concave top surface adapted to accept the back of the patient's head. Those skilled in the art will appreciate that any type of head support or standard pillow may be used in place of the optional head support 16 to the same effect.

The support system 10 may be provided in different sizes to conform to different body types and sizes. For example, the cradle, bolster, optional mat and optional head support may be provided in one or more of small, medium, large, extra large, and double extra large sizes. The system components may further be provided in separate small, medium, large, extra large, and double extra large sizes for men and women. For example, the different sizes may be scaled versions of the same components (e.g., a small size may include all components scaled to be 20% smaller than a large size). Typical dimensions for large size system components may include an arm cradle 12 in which the first, second and third sections 30, 32, and 34 measure approximately 42 cm overall, a side bolster 14 that may be approximately 48 cm, and a mat 18 that may be approximately 80×60 cm.

A further example embodiment of an arm cradle in accordance with the present invention is shown in FIGS. 9-13. This example embodiment of the arm cradle may be used with or without the mat 18, side bolster 14, or head support 16 discussed above. Although the present invention relates to an arm cradle for holding and stabilizing an arm of a post-operative shoulder surgery patient, those skilled in the art will appreciate that the arm cradle can be used for patients recovering from a variety of arm and shoulder injuries or surgeries.

Figure 9:
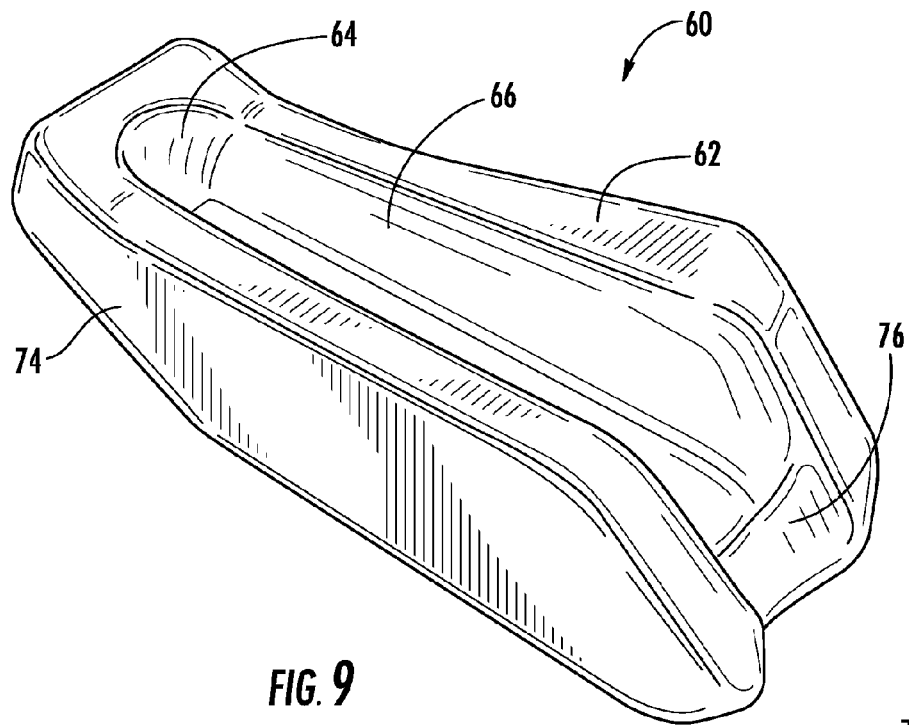
FIG. 9 shows an example embodiment of an arm cradle in accordance with the present invention (without a cover)
Figure 10:
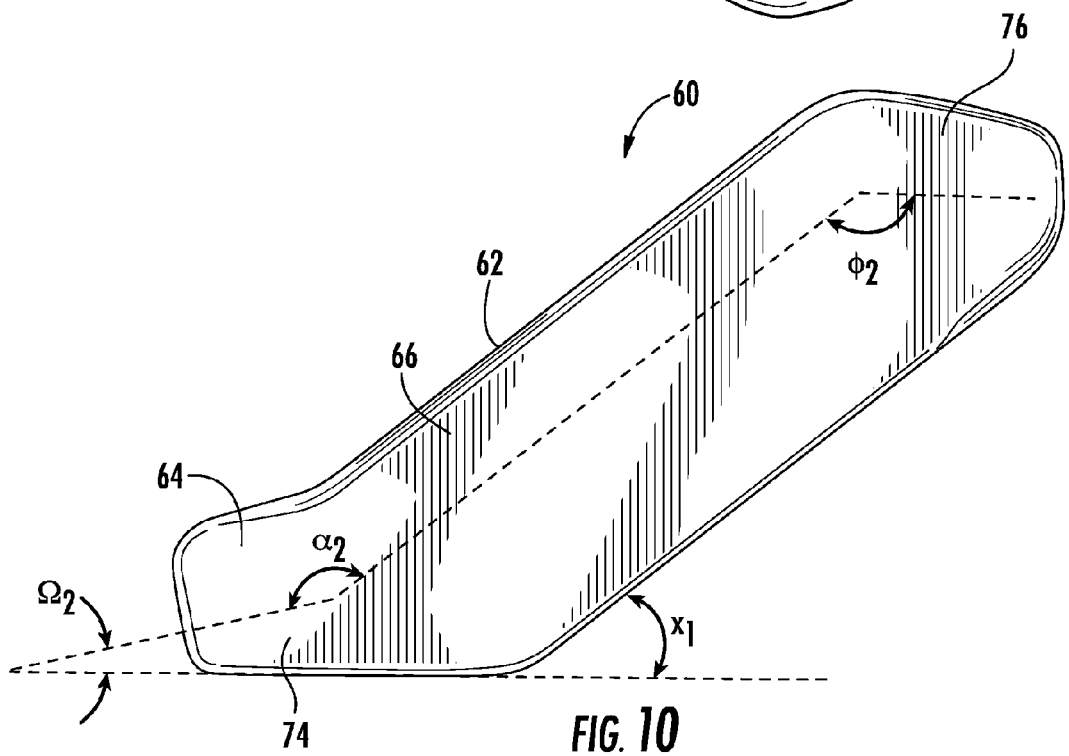
FIG. 10 shows a side view of the arm cradle of FIG. 9.

In one example embodiment of an arm cradle 60 as shown in FIG. 9, the arm cradle 60 may comprise a cradle body 62 having a first concave section 64 adapted to accept at least a portion of an upper arm of a patient and a second concave section 66 adapted to accept at least a portion of a lower arm of the patient. The first concave section 64 and the second concave section 66 may be arranged at an obtuse angle $\alpha_2$ with respect to one another (FIG. 10).

Figure 11:
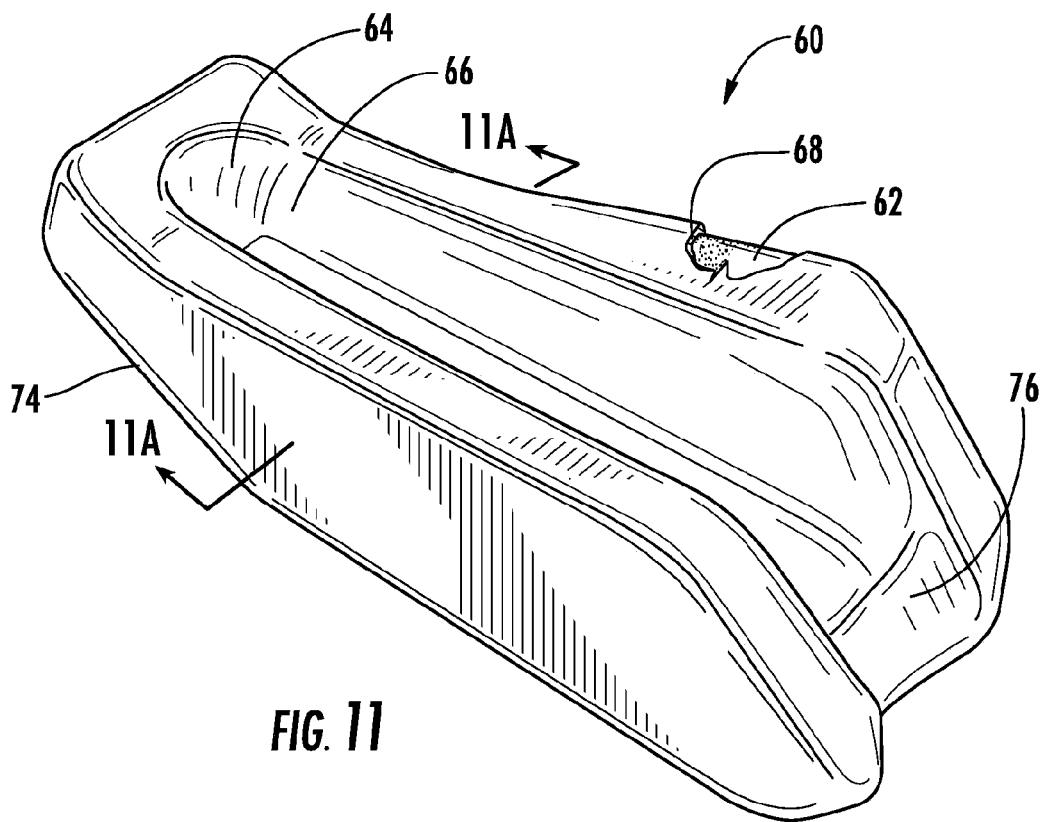
FIG. 11 shows an example embodiment of an arm cradle in accordance with the present invention with a cover.
Figure 11A:
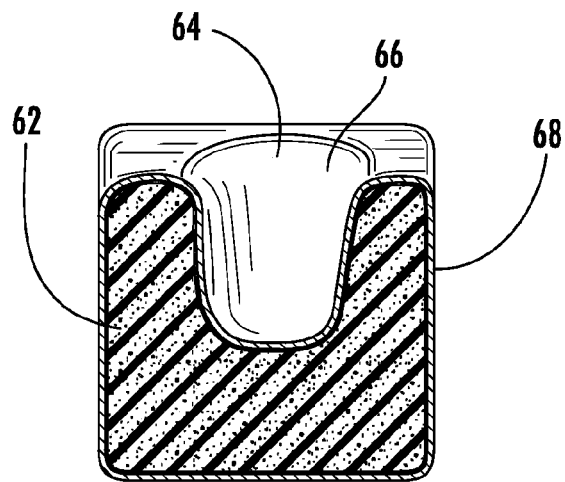
FIG. 11A is a sectional view through line 11A of FIG. 11.

A fabric cover 68 may be provided which is contoured to and covers the cradle body 62. FIGS. 11 and 11A show the arm cradle 60 with the fabric cover 68 in place. The remaining Figures show the arm cradle 60 without the fabric cover for clarity.

Figure 12:
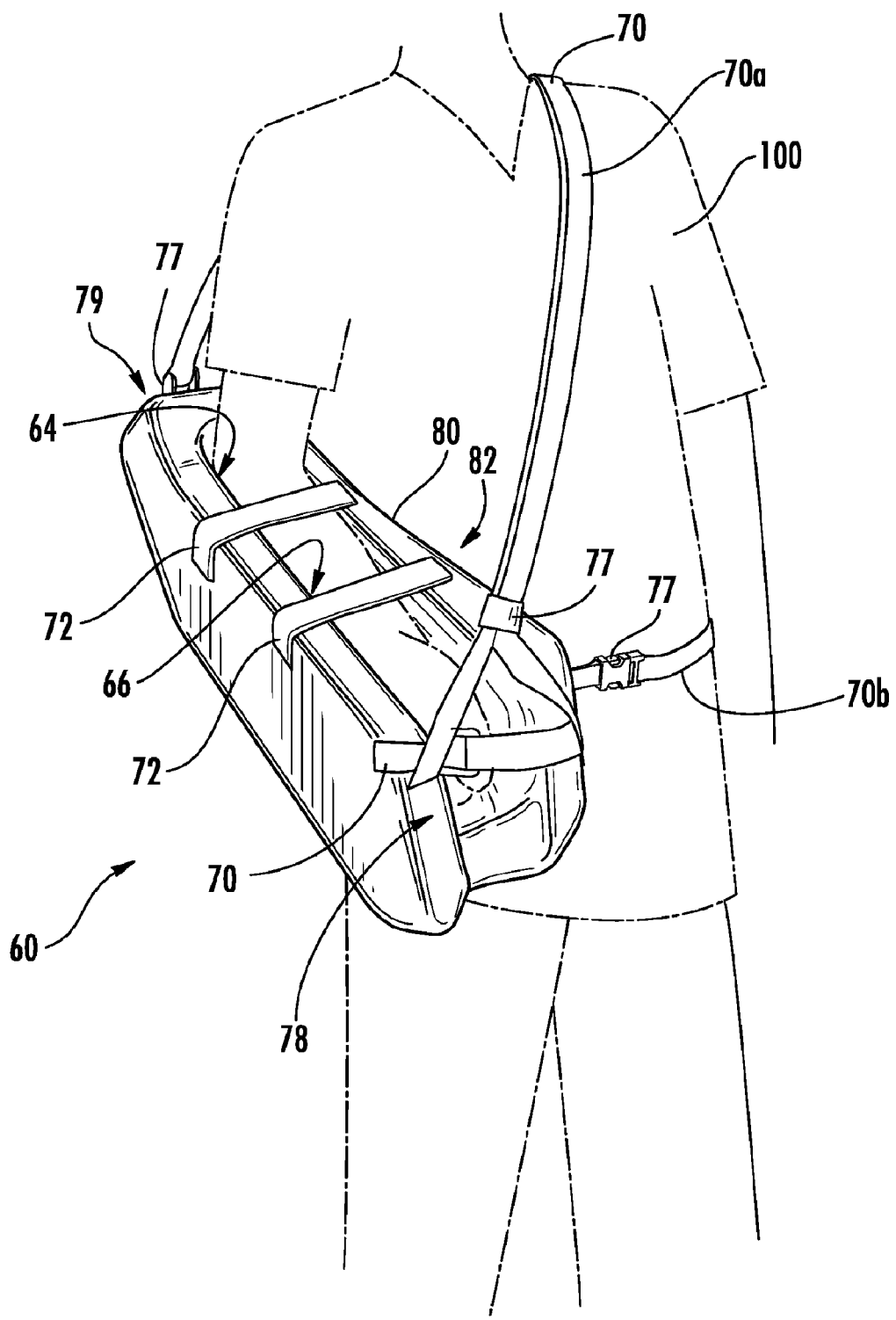
FIG. 12 shows an example embodiment of the arm cradle of the present invention being worn as a sling.

As shown in FIG. 12, one or more straps 70, 72 may be affixed to one of the cradle body 62 or the fabric cover 68 and used to secure the arm cradle 60 to the patient 100 and/or to secure the arm of the patient 100 in the arm cradle as discussed in more detail below. The straps are not shown in the remaining Figures for clarity.

The arm cradle 60 may be designed to at least partially encompass the upper and lower arms of the patient (e.g., so that the upper and lower arms, or at least portions thereof, sit down inside the cradle body 62 and are cushioned and protected by the concave sections). For example, the first concave section 64 of the arm cradle 60 may be of a depth corresponding to at least one-half to at least three-quarters of a diameter of the upper arm of the patient. The second concave section 66 may be of a depth corresponding to at least one-half to at least three-quarters of a diameter of the lower arm of the patient. Thus, as a result, the patient's arm sits down within the cradle, providing better stability and protection for the arm during recovery from surgery or injury.

The fabric cover 68 is removable. For example, the fabric cover 68 may be provided with a zipper or other fastening means (such as Velcro®, snaps, or the like) to enable it to be removed for washing or replacement.

The cradle body 62 may be comprised of a resilient foam material. For example, the cradle body 62 may be produced in one-piece via injection molding or hot-knife machined from a block of resilient foam material.

In a further example embodiment of the present invention, the arm cradle 60 may further comprises a base portion 74. The first concave section 64 may be angled with respect to the base portion 74. The first concave section 64 may be at an angle $\Omega_2$ in a first range between 0 and 30 degrees with respect to the base portion. The obtuse angle $\alpha_2$ between the first concave section 64 and the second concave section 66 may be in a second range between 90 and 170 degrees.

The cradle body 62 may further comprise a third concave section 76 adapted to accept at least a portion of a hand of the patient. The third concave section 76 may be of a depth corresponding to at least one-half to at least three-quarters of a thickness of the hand of the patient. The third concave section 76 may be angled with respect to the second concave section 66. For example, the third concave section 76 may be at an angle $\phi_2$ in a third range between 120 and 150 degrees with respect to the second concave section 66.

The cradle body 62 may be adapted to hold the arm of the patient at an angle when the patient is in a supine position and adapted to be worn as a sling when the patient is ambulatory. This is achieved by providing the base portion 74 with a flat bottom adapted to abut against one of a bed, a floor, a mat, or a flat surface when the patient is in the supine position (e.g., similar to that of arm cradle 12 shown in FIG. 1). For example, as shown in FIG. 10, due to the angle $\Omega_2$ between the base portion 74 and the first concave section 64 and the angle $\alpha_2$ between the first and second concave sections 64 and 66, the arm of the patient may be held at an angle $X_1$ with respect to the bed, floor, mat or other flat surface when in the supine position. As can be seen from the figures, the arm cradle 60 is designed to hold the arm such that the shoulder is in a position of neutral rotation (i.e., the angles between the sections 64 and 66 are such that the upper and lower arms are held in a plane that is perpendicular to the bed, floor, or other flat surface).

As shown in FIG. 12, the one or more straps 70, 72 may comprise one or more first straps 72 for securing the arm of the patient 100 in the arm cradle 60, and one or more second straps 70 for securing the arm cradle 60 to the patient 100.

The one or more first straps 72 may comprise at least one strap bridging opposite sides of the second concave section 66.

The one or more second straps 70 may comprise a shoulder strap 70a with one strap end affixed to a front section 78 of the arm cradle 60 and a second strap end affixed to a rear section 79 of the arm cradle 60, the shoulder strap 70a having an adjustable length sufficient to loop over a shoulder of the patient 100. The length of the strap 70a may be adjusted via buckles 77 as is well-known in the art. The one or more second straps 70 may further comprise an adjustable waist strap 70b adapted to encircle the waist of a patient 100.

Figure 13:
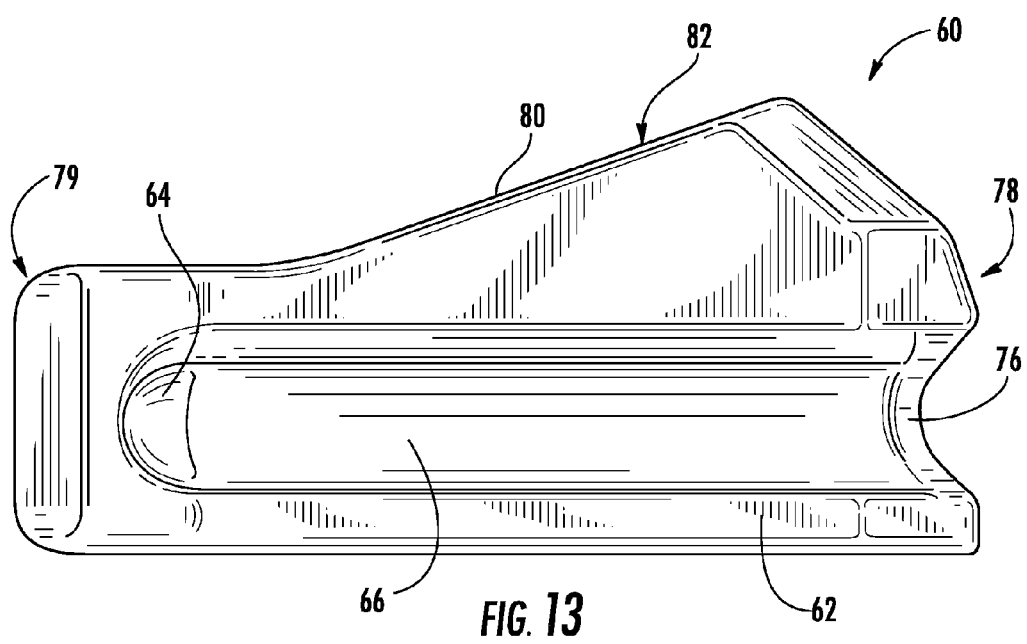
FIG. 13 shows a top plan view of the arm cradle of FIG. 9.

As shown in FIGS. 12 and 13, an inner side 80 of the cradle body 62 abutting a body of the patient 100 may be contoured to conform to the body of the patient 100. A portion 82 of the inner side 80 of the cradle body 62 may progressively widen from a back section 79 of the cradle body 62 towards a front section 78 of the cradle body 62.

The arm cradle 60 may be provided in different sizes to conform to different body types and sizes. Further, the arm cradle may be provided with a version adapted for a left arm of the patient with an inner side 80 contoured to conform to a left side of a patient and another version adapted for a right arm of a patient with an inner side 80 contoured to conform to a right side of a patient.

In order to secure the arm of the patient in the arm cradle 60, at least a portion of the upper arm is positioned in the first concave section 64 and at least a portion of the lower arm is positioned in the second concave section 66. The hand may be positioned in the optional third concave section 76 if provided. The arm cradle 60 can then be secured to the patient (and/or the arm of the patient can be secured in the arm cradle) using the straps 70, 72 provided.

It should now be appreciated that the present invention provides an advantageous systems, apparatus, and methods for supporting a patient's arm enabling shoulder surgery patients to sleep in a reclined position in a stable manner and which includes an arm sling adapted to be worn in a standing position during waking hours.

Although the invention has been described in connection with various illustrated embodiments, numerous modifications and adaptations may be made thereto without departing from the spirit and scope of the invention as set forth in the claims.

What is claimed is:

1. An arm cradle, comprising:
   a cradle body having a first concave section adapted to accept at least a portion of an upper arm of a patient and a second concave section adapted to accept at least a portion of a lower arm of the patient;
   the first concave section and the second concave section being arranged at an obtuse angle with respect to one another and adapted to maintain a shoulder of the patient in a position of neutral rotation;
   the first concave section having a longitudinal axis that is coplanar with a longitudinal axis of the second concave section along a plane that is perpendicular to a base portion of the arm cradle;
   a fabric cover for the cradle body, the fabric cover being contoured to and completely covering the cradle body; and
   one or more straps affixed to one of the cradle body or the fabric cover.

2. An arm cradle in accordance with claim 1, wherein:
   the first concave section is of a depth corresponding to at least one-half to at least three-quarters of a diameter of the upper arm of the patient.

3. An arm cradle in accordance with claim 1, wherein:
   the second concave section is of a depth corresponding to at least one-half to at least three-quarters of a diameter of the lower arm of the patient.

4. An arm cradle in accordance with claim 1, wherein:
   the fabric cover is removable.

5. An arm cradle in accordance with claim 1, wherein:
   the cradle body is comprised of a resilient foam material.

6. An arm cradle in accordance with claim 1, wherein:
   the first concave section is angled with respect to the base portion.

7. An arm cradle in accordance with claim 6, wherein:
   the first concave section is at an angle in a first range between 0 and 30 degrees with respect to the base portion; and
   the obtuse angle between the first concave section and the second concave section is in a second range between 90 and 170 degrees.

8. An arm cradle in accordance with claim 6, wherein:
   the cradle body is adapted to hold the arm of the patient at an angle when the patient is in a supine position and adapted to be worn as a sling when the patient is ambulatory.

9. An arm cradle in accordance with claim 8, wherein:
   the base portion has a flat bottom adapted to abut against one of a bed, a floor, a mat, or a flat surface when the patient is in the supine position.

10. An arm cradle in accordance with claim 1, wherein:
    the cradle body further comprises a third concave section adapted to accept at least a portion of a hand of the patient.

11. An arm cradle in accordance with claim 10, wherein:
    the third concave section is of a depth corresponding to at least one-half to at least three-quarters of a thickness of the hand of the patient.

12. An arm cradle in accordance with claim 11, wherein:
    the third concave section is angled with respect to the second concave section.

13. An arm cradle in accordance with claim 12, wherein:
    the third concave section is at an angle in a third range between 120 and 150 degrees with respect to the second concave section.

14. An arm cradle in accordance with claim 1, wherein:
    the one or more straps comprise:
    one or more first straps for securing the arm of the patient in the arm cradle; and
    one or more second straps for securing the arm cradle to the patient.

15. An arm cradle in accordance with claim 14, wherein:
    the one or more first straps comprise at least one strap bridging opposite sides of the second concave section.

16. An arm cradle in accordance with claim 14, wherein:
    the one or more second straps comprise a shoulder strap with one strap end affixed to a front section of the arm cradle and a second strap end affixed to a rear section of the arm cradle, the shoulder strap having an adjustable length sufficient to loop over a shoulder of the patient.

17. An arm cradle in accordance with claim 16, wherein:
    the one or more second straps further comprises an adjustable waist strap adapted to encircle the waist of the patient.

18. An arm cradle in accordance with claim 1, wherein:
    an inner side of the cradle body abutting a body of the patient is contoured to conform to the body of the patient.

19. An arm cradle in accordance with claim 18, wherein:
    a portion of the inner side of the cradle body progressively widens from a back section of the cradle body towards a front section of the cradle body.

20. A method for supporting an arm of a patient, comprising:

provplaceholderiding a cradle body having a first concave section adapted to accept at least a portion of an upper arm of the patient and a second concave section adapted to accept at least a portion of a lower arm of the patient, with the first concave section and the second concave section being arranged at an obtuse angle with respect to one another and adapted to maintain a shoulder of the patient in a position of neutral rotation, the first concave section having a longitudinal axis that is coplanar with a longitudinal axis of the second concave section along a plane that is perpendicular to a base portion of the arm cradle;

providing a fabric cover for the cradle body, the fabric cover being contoured to and completely covering the cradle body;

providing one or more straps affixed to one of the cradle body or the fabric cover;

positioning at least the portion of the upper arm in the first concave section;

positioning at least the portion of the lower arm in the second concave section; and securing the arm cradle to the patient.

* * * * *